United States Patent [19]

Ayers

[11] Patent Number: 5,024,235
[45] Date of Patent: Jun. 18, 1991

[54] ELECTROENCEPHALIC NEUROFEEDBACK APPARATUS AND METHOD FOR BIOELECTRICAL FREQUENCY INHIBITION AND FACILITATION

[76] Inventor: Margaret A. Ayers, 10623 Bloomfield, Toluca Lake, Calif. 91602

[21] Appl. No.: 484,824

[22] Filed: Feb. 26, 1990

[51] Int. Cl.$^5$ .......................................... A61B 5/0482
[52] U.S. Cl. ..................................... 128/732; 128/905
[58] Field of Search ............... 128/731, 732, 905, 733; 600/26, 28

[56] References Cited

U.S. PATENT DOCUMENTS

| | | | |
|---|---|---|---|
| 3,821,949 | 7/1974 | Hartzell et al. | 128/732 |
| 3,967,616 | 7/1976 | Ross | 600/27 |
| 4,354,505 | 10/1982 | Shiga | 128/732 |
| 4,407,299 | 10/1983 | Calver | 128/732 |
| 4,632,126 | 12/1986 | Aguilar | 128/732 |
| 4,800,893 | 1/1989 | Ross et al. | 128/732 |

*Primary Examiner*—Francis Jaworski
*Assistant Examiner*—George Manuel

[57] ABSTRACT

An improved method and apparatus for displaying and either inhibiting or promoting selected bioelectrical frequencies emitted by a living organism. The method includes the steps of detecting an analog bioelectrical signal, converting the signal to discrete digital signals representing corresponding frequencies and numerically analyzing the digital signals to determine the different bioelectrical frequencies emitted by the organism. Furthermore, a threshold amplitude associated with a selected digital signal can be established an auditory or visual signal can be sent to the organism to indicate whether the bioelectrical frequency under study is within or outside the threshold amplitude. With this information the organism can be taught to inhibit or facilitate the bioelectrical frequency. The apparatus comprises a pair of electrodes, an analog signal amplifier, an analog to digital converter, a selector to select a frequency of interest, a display monitor, and a computer to distinguish the digital signals as different frequencies, display the frequencies, and determine when the frequency is falling inside or outside a predetermined range. Also, a magnetic medium recording device is used to capture data. Finally, a lighting or sounding circuit is used to tell the organism whether the frequency under study is being inhibited or facilitated.

12 Claims, 4 Drawing Sheets

ABSTRACT# ELECTROENCEPHALIC NEUROFEEDBACK APPARATUS AND METHOD FOR BIOELECTRICAL FREQUENCY INHIBITION AND FACILITATION

BACKGROUND OF THE INVENTION

The invention relates in general to the reception and processing of bioelectrical signals from an organism. Furthermore, the invention relates to an improved method and apparatus for receiving bioelectrical signals, processing the signals and signaling back to the organism so as to allow the organism to either inhibit or facilitate a selected frequency.

A number of different feedback-type methods and apparatus are known dating back to as early as 1960. Early studies by several researchers focused on bioelectrical feedback on persons suffering from hemiplegia, i.e., paralysis of one lateral half of the body resulting from injury to the motor centers of the brain.

In 1960, A. A. Marinacci and M. Horande investigated neurofeedback with respect to left-sided hemiplegia. As reported in "Electromyogram in Nueromuscular Re-education", *Bulletin of the Los Angeles Neurologic Society*, 25: 57-71, 1960, they inserted needle electrodes into the involved left arm muscles, and could find no voluntary nerve impulses. Electrodes were inserted into the normal right deltoid to show the patient how muscle activity could produce auditory feedback. The electrodes were then inserted into the paralyzed left deltoid muscle. The patient was able to generate from 10 to 15 percent motor action potential in a location from which there had been no previous detectable activity. The same procedure was utilized successfully at other muscle sites.

In 1964, J. M. Andrews reported on study utilizing a patient group of hemiplegics who had electromyogram EMG electrodes inserted in the involved tricep muscles as reported in "Neuromuscular Re-education of the Hemiplegic with the Aid of the Electromyograph," *Archives of Physical Medicine and Rehabilitation*, 45: 530-532, 1964. Auditory feedback was provided as the subjects tried to generate sound and movement. A five-minute trial period was allowed, and seventeen out of the twenty patients showed an increase in motor action potentials.

In 1973, H. E. Johnson and W. E. Garton reported on ten hemiplegic patients, who utilized EMG practices as an aid in total rehabilitation rather than just the return of voluntary movement as in the Andrews study as discussed in "Muscle Re-education in Hemiplegia by use of Electromyograph Device", *Archives of Physical Medicine and Rehabilitation*, 54: 320-325, 1973. Five out of ten subjects had enough improvement to eliminate leg bracing on the involved side.

In 1974, J. Brudny and others used EMG feedback to treat a group of thirty-six patients, thirteen of whom had hemiparesis. Brudny, J. Korein, J., Levidow, L. Grynbaum, B. B., Lieberman, A., and Friedman, L. W., "Sensory Feedback Therapy as a Modality of Treatment in Central Nervous Disorders of Voluntary Movement," *Neurology*, 24: 925-932, 1974. In this study surface electrodes were used instead of inserted needle electrodes. In two individuals there was no change. In one patient there was relief from muscle spasticity. In six patients function of the extremity was re-established, and in four cases prehension became possible.

Also, in 1974, D. Swaan, P. C. W. Van Wieringer and S. D. Fokkema explored EMG feedback of seven patients, four of whom were hemiplegic. "Auditory Electromyographic Feedback Therapy to Inhibit Undesired Motor Activity," *Archives of Physical Medicine and Rehabilitation*, 57:9-11, 1974. The subjects taught to inhibit the peroneus longus muscle while contracting their quadricep muscle. Conventional rehabilitation methods were used to suppress the undesirable hyperactivity of the peroneus longus muscles along with the feedback. No justification was given for reinforcement of the quadriceps and inhibition of the peroneus longus.

In 1975, J. V. Basmajian, C. G. Kukulka, M. G. Narayan and K. Takebe compared EMG biofeedback plus physical therapy with the results of standard rehabilitation procedures in cases of ankle dorsiflexion paralysis after stroke repeated in "Biofeedback Treatment of a Foot-Drop After Stroke Compared With Standard Rehabilitation Techniques: Effects on Voluntary Control and Strength," *Archives of Physical Medicine and Rehabilitation*, 56: 231-236, 1975. The authors claimed that an increase in both strength and range of motion in the biofeedback group was twice as great as the achievements of the exercise control group. The two groups of patients were not variably matched. When biofeedback was added to physical therapy, the mixed variables were not controlled.

In 1976, L. P. Taylor and B. Bongar described the use of electromyometry feedback for the treatment of cerebrovascular lesion patients in *Clinical Applications in Biofeedback Therapy*, Psychology Press, Los Angeles, Calif., 1976. Patients were taught to inhibit one set of muscles while simultaneously facilitating others. For example, inhibition of thumb flexion was attempted while thumb extension was facilitated.

In 1979, F. Keefe and K. Trombly utilized EMG feedback to aid a hemiplegic patient judge limb position without being able to see the limb in "Impaired Kinesthetic Sensation: Can EMG Feedback Help?" Presented at the Proceedings of Biofeedback Society of America, Tenth Annual Meeting, February, 1979 in San Diego, Calif. The patient participated in an A-B-A-B withdrawal design to evaluate the effects of EMG biofeedback on accurate limb positioning. EMG feedback with audio feedback produced improvement in performance relative to baseline. Withdrawal of feedback produced a decrement in performance, and when EMG feedback was re-instituted, performance once again improved. The patient was able to generalize the EMG feedback training to improved functional use of the arm.

In 1979, R. Koheil, et al, at the Ontario Crippled Children Centre, developed a Joint Position Trainer to provide precise feedback of limb position to three hemiplegics. Koheil, R., Mandel, A., Herman, A. and Iles, G., "Joint Position Training for Hyperextension of the Knee in Stroke Patients: Preliminary Results", presented at the Proceedings of the Biofeedback Society of America, Tenth Annual Meeting, February, 1979 in San Diego, Calif. The Joint Position Trainer provided feedback of position rather than of muscle activity, and incorporated a goniometer attached to a leg cuff with auditory feedback of knee joint angle. Two of the three patients developed improved gait with increased control of knee hyperextension.

The results of the techniques involved had limited results because the difficulty of recognizing particular frequencies generated which could not be readily determined, nor could the subject have the ability to control these frequencies.

Other research efforts were conducted specifically upon those bioelectrical signals emanating from the brain. One of the earlier works was written in 1966 by T. Mullholland and C. R. Evans who described the use of alpha waves (approximately 7.5-11.5 Hertz) emanating from the brain to drive a feedback signal that could be perceived by the test subject and induce relaxation. Mulholland, T., and Evans, C. R., *Nature*, 211: 1278, 1966. The alpha waves could be controlled to some degree by the test subject's recognition of a tone or light when alpha waves were produced. Similarly, differentiation of particular frequencies of bioelectrical signal prevented the test subject from readily acknowledging and either inhibiting or facilitating particular frequencies.

Other electroencephalograph (EEG) feedback devices are described in publications by Spunda, J. and Radil-Weiss, T., "A Simple Device for Measuring the Instaneous Frequency of the Dominant EEG Activity", *Electroencephalographic Clinical Neurophysiology*, 32: 434, 1972. This device converted EEG frequencies into voltage levels for analysis using bandpass analysis. A series of wave form generators were activated by the flip-flop at each positively directed zero point of the filtered signal resulting in a voltage level corresponding to the frequency.

Another EEG feedback device was described in Hicks, R. G., and Angner, E., "Instrumental evaluation of EEG Time Relationships", *Psychophysiology*, 6:44, 1970. This device analyzed minute time displacements of EEG waves from cortical waves using peak detection and a type of logic as a feedback device.

Also, in Boudrot, R., "An Alpha Detection and Feedback Control System", *Psychophysiology*, 9:467, 1972, a feedback device picked up alpha waves and provided auditory and visual stimulus feedback to the patient. Then, in Pfeifer, E. A., and Usselmann, C., "A Versatile Amplitude Analyzer for EEG Signals to Provide Feedback Stimuli to the Subject", *Med. Biol. Eng.* 8: 309, 1970, a feedback device analyzed the amplitude and provided feedback cues to subjects in studies of EEG modification. It allowed for usage with bandpass analysis incorporating logic components and a display.

Additionally, U.S. Pat. No. 3,837,331 to Sidney A. Ross, issued Sept. 24, 1974, entitled "System and Method for Controlling the Nervous System of a Living Organism" describes an apparatus and method for determining particular frequencies of a bioelectric signal which is analog by nature. The Ross device like the other devices require the use of band pass analysis or other techniques to filter out particular frequencies to study a particular frequency of interest.

In band pass analysis, analog filters analyze how much frequency is produced in a given period of time, or a frequency in relationship to time and voltage. The apparatus required includes a precision attenuator, an active band pass filter, a rectifying means and an integrating means in addition to those components normally utilized in bioelectrical feedback devices. Furthermore, band pass analysis or power spectral analysis is necessary to isolate the particular frequency of interest. Such analysis is typically performed on a large computer requiring special analytical skills and extensive computing time. Power spectral analysis looks at the variance of a bioelectrical signal or the covariance between one or more signal channels. The signal is broken into different frequency bands in relationship to the power density which is then analyzed using a fourier series program.

Not only is the above approach burdensome and time consuming, but also inaccurate. The frequency results are often distorted because the analytical approach used is based on exponential and logrithic analysis. Determining the actual frequency desired to inhibit or facilitate is at best haphazard due to the margins for error in the above approach.

Also, the above referenced devices lack suitable means for displaying and recording the changing frequencies under study for subsequent review and manipulation for purposes of analysis. But, most importantly, these EEG feedback devices lacked the ability to establish selected limits or thresholds in which to gauge the progress of a test subject or reward the test subject once the test subject learned to inhibit or facilitate a particular frequency of interest.

The above-mentioned deficiencies are overcome by the present invention. There is a great interest in the neuropsychology and neurophysiology community for such a device which overcomes these deficiencies. Researchers and practitioners should recognize the value immediately of the present invention. Furthermore, persons suffering from nervous disorders, induced by trauma, drug use or cogenital aberration can greatly benefit from the present invention. The present invention operates as a diagnostic tool, as well as, a means for curing nervous disorders or abnormalities in the body, particularly the brain.

SUMMARY OF THE INVENTION

The invention includes two embodiments of a method and two embodiments of an apparatus for practicing the methods, respectively.

The first method is an improved method of detecting and displaying analog bioelectrical frequencies in an organism's or person's body comprising the steps of detecting an analog bioelectrical signal at a selected location in the person's body, amplifying the analog bioelectrical signal, converting the analog bioelectrical signal to digital signals representing particular frequencies, and selecting a particular digital signal of interest and displaying and/or recording the particular signal of interest in the form of a continuous waveform over time.

The apparatus used to perform the above method comprises a receptor means for attachment to the selected location of the person or organism for receiving an analog bioelectrical signal, an amplifier for amplifying the analog bioelectrical signal received by the receptor means and associated therewith, and an analog to digital converter for converting the analog bioelectrical signal to digital signals representing corresponding electrical frequencies. The converter receives the amplified analog bioelectrical signal from the amplifier.

A computer is used for integrating amplitude of one of the digital signals over a predetermined duration and dividing a resulting value by voltage to determine a change in voltage with respect to time duration, and thereby determine electrical frequencies emitted by the person or organism. The computer then converts the resulting value divided by voltage to a format which can be plotted over time. A display monitor for displaying the prescribed format of the corresponding electrical frequencies can be incorporated.

Furthermore, a magnetic disk recorder for recording the resulting value divided by voltage over time is used to record the information for subsequent review or analysis.

The second embodiment of the method of the invention involves the first embodiment of the method described above. Additional steps include sending a signal to the person when the particular digital signal of interest falls within a selected amplitude threshold for a predetermined duration, and causing the person to mentally concentrate so as affect the amplitude of the particular digital signal of interest. This allows the person to affect a certain corresponding analog bioelectrical frequency emitted at the selected location of the person's body.

Subsequent to the step of establishing an amplitude for the particular digital signal, an additional step may include integrating the amplitude of the selected digital signal with respect to duration and dividing by the amplitude threshold voltage. This yields a determination of whether voltage of the selected digital signal is changing, and thereby whether the corresponding analog bioelectrical frequency is being inhibited or accentuated.

Also, another step may be added by displaying the selected digital signal as a continuous waveform and displaying the voltage thresholds as horizontal lines associated with the continuous waveform to facilitate the determination of whether the corresponding analog bioelectrical frequency is being inhibited or facilitated.

Similarly, a step of recording may be added where the digital signals are recorded to a magnetic medium for review and data manipulation.

The step of continuously displaying the particular digital signal of interest as a waveform changing with respect to time can be incorporated wherein the amplitude threshold voltage is displayed as a straight line.

A step of suppressing exteraneous signals unrelated to the analog bioelectrical signal of interest may be used to suppress unwanted noise.

The apparatus used in the second embodiment is similar to that apparatus described above. The step of detecting an analog bioelectrical signal is achieved by using two electrodes positioned at the selected location of the person's body to be affected. The step of amplifying is achieved by using a signal amplifier associated with the electrodes and which recognizes voltage potential between the electrodes. The step of converting is achieved by receiving signals representing voltage variations over time and using an analog to digital converter to convert voltage variations into digital pulses.

The step of selecting is achieved using a numerical analyzer to select digital pulses corresponding to particular analog bioelectrical frequencies. The step of sending is achieved by use of a light or sound to the person when the analog bioelectrical frequency recognized between the electrodes falls within a predetermined range for a predetermined duration. The step of displaying is achieved using a waveform scroller for displaying particular digital signals as a continuous wave over time and using a monitor for displaying the continuous wave over time as plotted by the waveform scroller. The step of integrating is achieved using a computer which can compute integrals.

Other aspects and advantages of the present invention will become apparent from the following description of the preferred embodiments, taken in conjunction with the accompanying drawings, which illustrate, by way of example, the principles of the present invention.

DESCRIPTION OF THE PREFERRED EMBODIMENT

Figure 3:
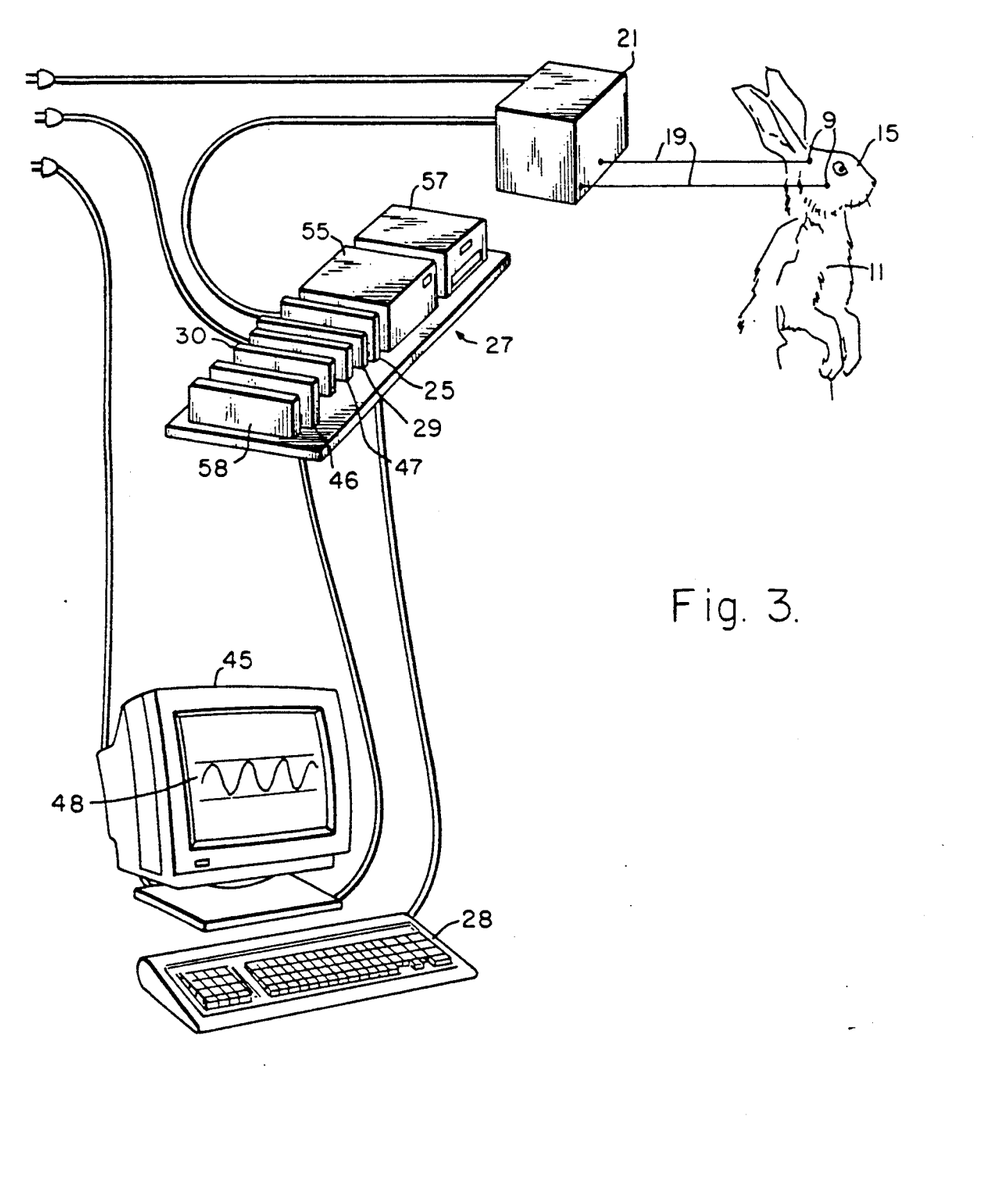
FIG. 3 is a top right perspective view of a first preferred embodiment of the improved apparatus of the present invention shown associated with a test subject.
Figure 4:
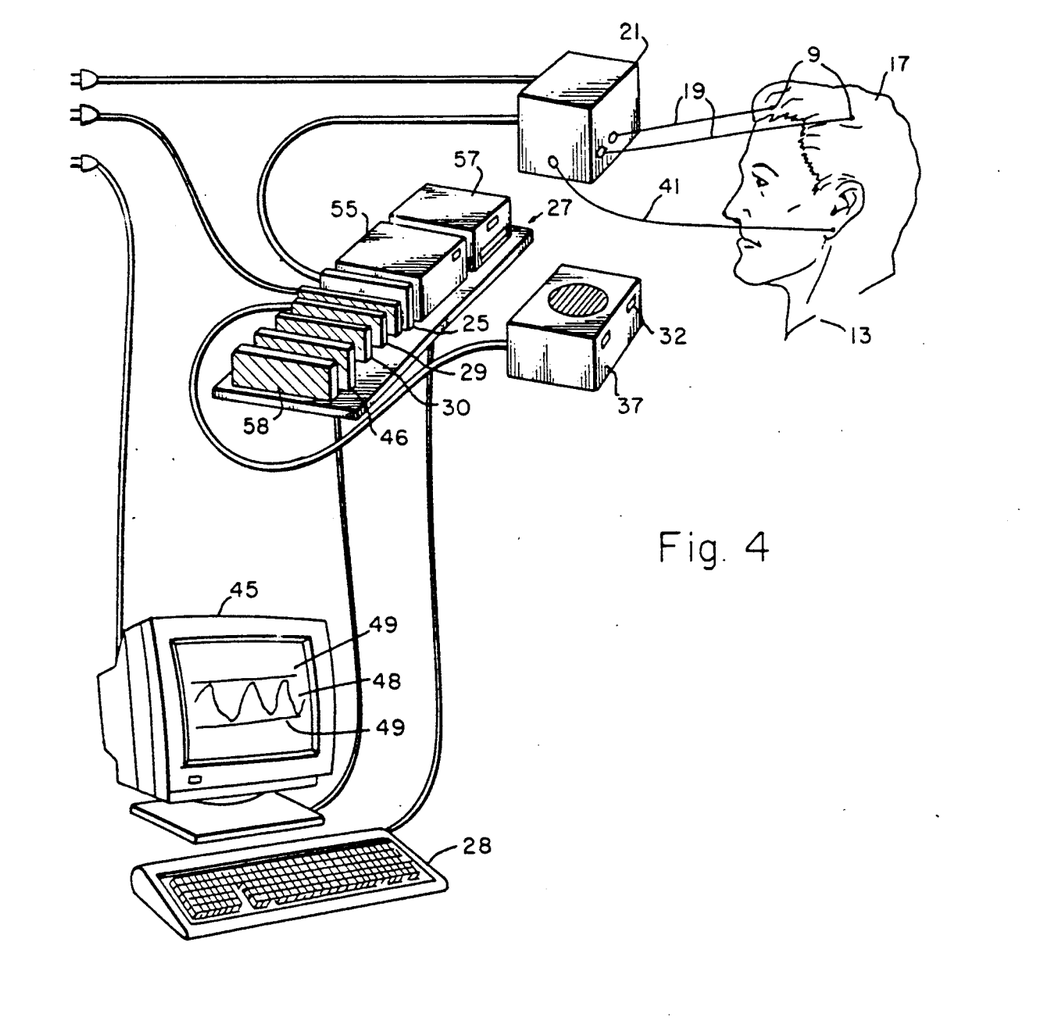
FIG. 4 is a top right perspective view of a second preferred embodiment of the improved apparatus of the present invention shown associated with a test subject.

As shown in the drawings, wherein like numerals represent like elements, an organism 5 can be monitored using a receptor means 7 as shown by the schematics of FIGS. 1–4. The receptor means 7 comprises at least two electrodes 9 of a ferrous materials shown attached to a rabbit 11 in FIG. 3 and a man 13 in FIG. 4. The electrodes 9 can be placed on any portion of the body where bioelectric signals may be of interest. As shown in FIGS. 3 and 4 the bioelectrical signals of the head 15 of the rabbit 11 and the head 17 of the man 13. Voltage potentials between the two electrodes 9 can be sensed over time and transmitted by wires 19 to an amplifying means or amplifier 21. One amplifier used is the morendocino microcomputer EEG amplifier or equivalent. The amplifier 21 is of a kind that can amplify analog signals such as bioelectrical signals produced by living organisms. Amplification is necessary because bioelectrical signals are typically vary faint and cannot be readily analyzed by electrical means. Such amplifiers are commonly known in the art of electroencephelgraphic applications.

Once the analog bioelectrical signal is sufficiently amplified, the signal can be digitized or demodulated by an analog to digital converter means 23 so as to produce discrete digital signals which correspond to the frequencies inherent in the analog bioelectric signal. Some signal filtering may be necessary to properly process the analog bioelectric signal prior to demodulation. Demodulation of the analog bioelectric signal can be achieved by using a DASH-16 an log/digital input card 25. The input card 25 is manufactured by Metrabyte Corp., and is a high speed multifunction analog/digital I/O expansion board for a personal computer.

The DASH-16 uses an industry standard (HI-674A) 12 bit successive approximation converter with a 12 microsecond conversion time giving a maximum throughput rate of 60 KHz in D.M.A. mode. The channel input configuration is switch selectable on the board, providing a choice between 16 single ended channels or 8 differential channels with 90 dB common mode rejection and ±10 v common mode range.

Analog to digital conversions may be initiated in any one of 3 ways, by software command, by internal programmable interval timer o by direct external trigger to the analog to digital. At the end of the analog to digital (A/D) conversion, it is possible to transfer the data by any of 3 ways, by program transfer, by interrupt or by D.M.A. All operating modes are selected by a control register on the DASH-16 and are also supported by its accompanying utility software.

High input impedance ranges of +1 v, +2 v, +5 v & +10 v unipolar and ±0.5 v, ±1 v, ±2.5 v, ±5 v & ±10 v bipolar are switch selectable. These ranges are common to all channels and are controlled by the gain of the input instrumentation amplifier. Other ranges may be realised with a single user installed resistor. All inputs are multiplexed through a low drift, fast settling instrumentation amplifier/sample-hold combination and the channel input configuration is switch selectable to operate as either 16 single ended or 8 differential channels.

A 3 channel programmable interval timer (Intel 8254) provides trigger pulses for the A/D at any rate from 250 KHz to 1 pulse/hr. 2 channels are operated in fixed divider configuration from an internal 1 MHz xtal clock (optional 10 MHz jumper selectable on DASH-16F). The third channel is uncommitted and provides a gated 16 bit binary counter that can be used for event or pulse counting, delayed triggering, and in conjunction with the other channels for frequency and period measurement.

2 channels of multiplying 12 bit D/A output. The D/A converters may be operated with a fixed −5 v reference available from the DASH-16 board to give a 0-+5 v output. Alternatively an external D.C. or A.C. reference may be used to give different output ranges or programmable attenuator action on an A.C. signal. D/A's are double-buffered to provide instantaneous single step update.

A −5 v (±0.05 v) precision reference voltage output is derived from the A/D converter reference. Typical uses are providing a D.C. reference input for the D/A converters and offsets and bridge excitation to user supplied input circuits.

Digital I/O consists a 4 bits of TTL/DTL compatible digital output and 4 bits of digital input. Apart from being addressed as individual I/O ports, some of the digital inputs do double duty in some modes as A/O trigger and counter gate control inputs.

The analog/digital input card 25 is incorporated within a modified personal computer 27 which can be of an IBM PC or XT type sufficient to interface with the analog/digital input card 25.

The digital signals resulting can be further analyzed with respect to certain analog bioelectric frequencies sensed. A selector means 29 allows sufficient manipulation of the digital signals so as to separate particular digital signals which correspond to the particular bioelectric analog frequencies to be monitored. This function can also be achieved by using the DASH-16 card.

The computer 27 comprises a 8087 numerical processor card 29 with an expanded memory card 30 which among other things allows the selection of particular digital signals of interest corresponding to the bioelectric frequency to be studied. Such a selection can be performed by digital separation using certain digital filters commonly known in the art of digital filtering. Many of these techniques can be implemented by use of the DASH-16 card.

Furthermore, a computing means 31 is used to integrate the amplitude of the particular digital signal over a predetermined duration. The resulting value is divided by microvoltage to determine a change in voltage with respect to time duration, and thereby determine the bioelectric frequencies emitted by the person or animal. This calculation is achieved by the computer 27 driven by particular algorithms which are herein disclosed and addressed in Appendix A attached hereto. Appendix A is a list of software variables and their interrelationships. The computer 27 with a keyboard 28 then converts the resulting values divided by micro voltage to a format which can be plotted over time. Threshold values can be entered by the keyboard 28 and established such that when the amplitude of the resulting signal is within a certain amplitude range (the bioelectric signal is within a particular frequency) a signaling means signals to the person an auditory, visual, or sensible signal indicating that bioelectric frequencies are within the pre-determined ranges. An amplitude sensing means 35 is used which may be a simple algorithm preset or varied by a technician or the subject coordinating the monitoring.

The signaling means 33 is simply a light box or sound box 37 that emits a sound or light or series of sounds or lights which indicate to the subject that the bioelectric frequencies received by the monitoring electrodes 9 are within a preset frequency range. Of course, the signaling means can also be any other type of stimuli that can be sensed by the subject. One approach considered is the use of a video type game displaying animations which can be controlled by way of controlling the brainwave frequencies.

Once the subject is aware that bioelectric frequencies within a certain range can be sensed, a feedback phenomenon is possible. The subject can be trained to focus mentally upon obtaining the stimuli from the signaling means 33 and thereby, alter the bioelectric frequencies produced at the location of the electrodes 9. Bioelectric frequencies of a predetermined kind can either be facilitated and produced more readily or inhibited once the subject can be alerted to whether those frequencies produced are within the preset range.

Furthermore, a suppression means 39 or artifact suppression device can be used to suppress unwanted signals that would normally trigger the signaling means 33. Unwanted signals include "noise" attributable to bioelectric activity in the subject's muscles. A bipolar hookup with an ear reference may be used incorporating baseline wire 41 connected to the subject's ear or other part of the body which provides a signal to the suppressing mean 33 which indicates that a comparable signal received from the electrodes 9 should be suppressed. The structure and function of the suppressed means 39 are commonly known in the art and are not further herein discussed. Suffice it to say that extraneous bioelectric frequencies not of interest emanating from a location not around the electrodes 9 can be suppressed. As shown in FIG. 4, the requisite suppression circuity can be found within the amplifier 21 or within the computer 27.

A display means 43 or monitor 45 can be used in conjunction with a waveform scroller display card 45 and a graphics display card 46 to display the demodulated and processed data resulting from the processed bioelectric signal. The graphics display card is a Hercules monochrome card, but a number of IBM compatible cards can be used. The waveform scroller card 45 is commonly known in the art of computer graphics for displaying data points over time on a monitor.

The particular frequency of interest is displayed as a sinosoidal wave 48 which changes amplitude depending upon whether the particular frequency of interest is being inhibited or facilitated. More particularly, the waveform scroller card 47 processes the data received by the computing means 31 and displays it on the monitor 45. The actual data displayed are the values of the integration of the digital signals of interest over time divided by microvoltage representing the particular frequencies of interest making up the bioelectric signal. Upper and lower threshold levels can be established and displayed on the display monitor 45 as horizontal lines 49. The horizontal lines 49 represent particular microvolt scales correlated to particular bioelectric frequencies. When the amplitude of the sinosoidal wave exceeds the limits imposed by the horizontal lines 49, the signaling means 33 or light or sound box 37 send a particular signal to the subject to indicate that a particular frequency is not being suppressed or inhibited. When the sinosoidal wave 48 is within the horizontal lines 49 the subject is sent a different signal indicating that the particular bioelectric frequency of interest is being inhibited at least within the microvolt levels defined by the horizontal lines 49. Upon practice by the subject, the horizontal lines 49 can be brought closer together representing a requirement that even less of a particular bioelectric frequency must be produced to achieve a reward response by the signaling means. Of course, the use or nonuse of lights or reward systems can be modified.

A timing means 51 comprising timing circuitry commonly known in the art can be used to time the required duration that the level of bioelectric frequency production must stay within proscribed limits before a reward signal is given. The duration can be lessened once the subject has improved his ability to inhibit the production of certain bioelectric frequencies. Variability of the duration is a feature which allows greater clinical and therapeutic customization of the invention depending on the particular subject encountered and the level of skill developed by the subject.

A recording means 53 can be used to record to a magnetic medium or hard disk 55, or floppy disk drive 57 to record on a floppy disk (not shown). If a hard disk 55 is used, a hard disk controller card 58 is necessary and commonly known in the art of magnetic recording medium. The therapy session results displayed on the display monitor 45 can be stored in a format to be displayed and compared with past sessions or to be compared with future sessions. A large variety of software tools commonly known in the art of statistical evaluation to compare the subject's progress in inhibiting or facilitating particular bioelectric frequencies can be used. Most helpful is compressing the waveform produced over the entire session to a format which can be viewed in its entirety on a screen or page of paper. Such analysis is helpful to see the subject's ability to inhibited or facilitate a particular frequency over the period of the entire therapy session. This information is not only helpful to the clinician, but also to the subject since the cognitive effect on the subject may enhance his or her ability to further facilitate or inhibit certain bioelectric frequencies.

Although feedback is primarily provided to the subject by the signaling means 33, the display means can be used by the subject to monitor his own progress in facilitating or inhibiting certain bioelectric frequencies.

Figure 1:
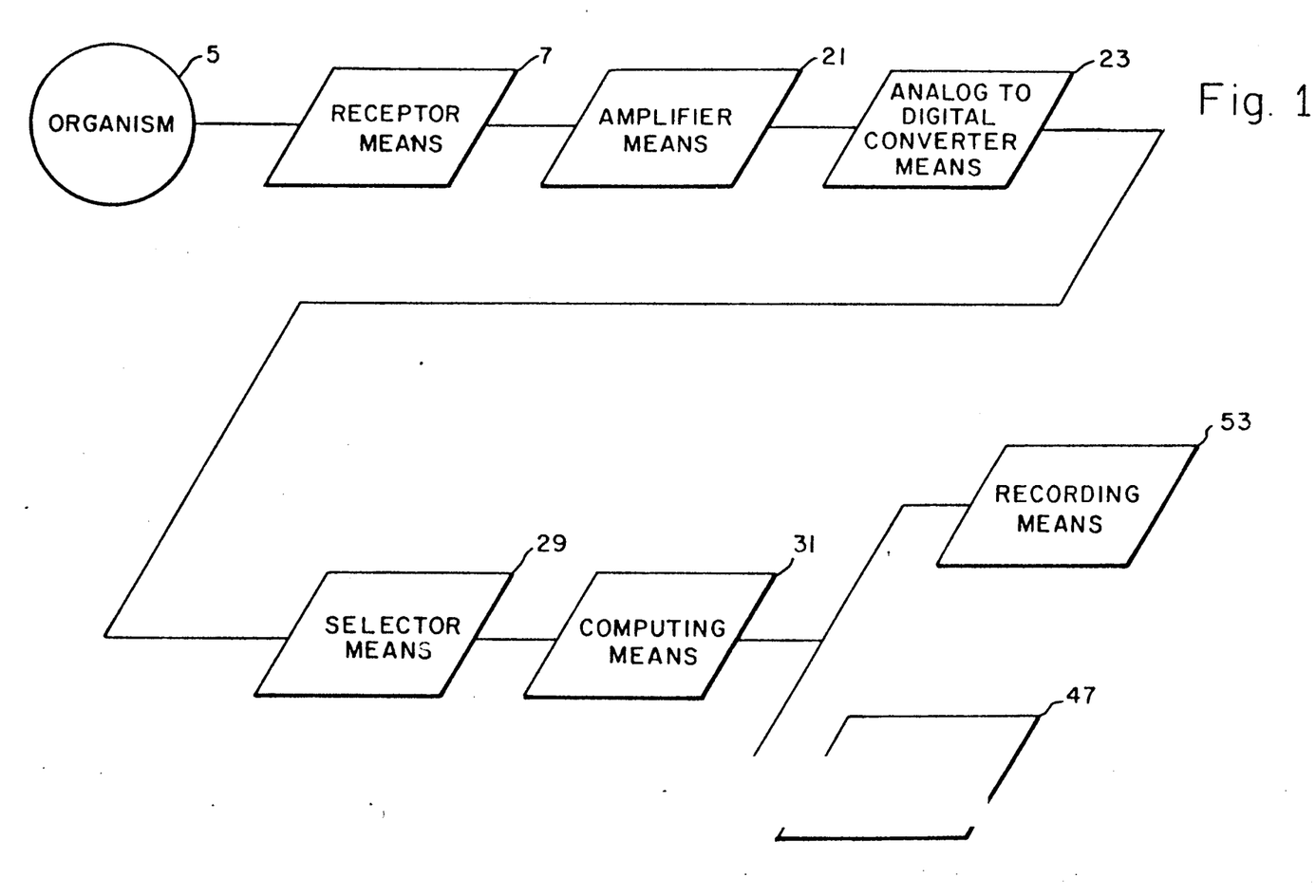
FIG. 1 is a functional block diagram of a first preferred embodiment of the improved method of the present invention.
Figure 2:
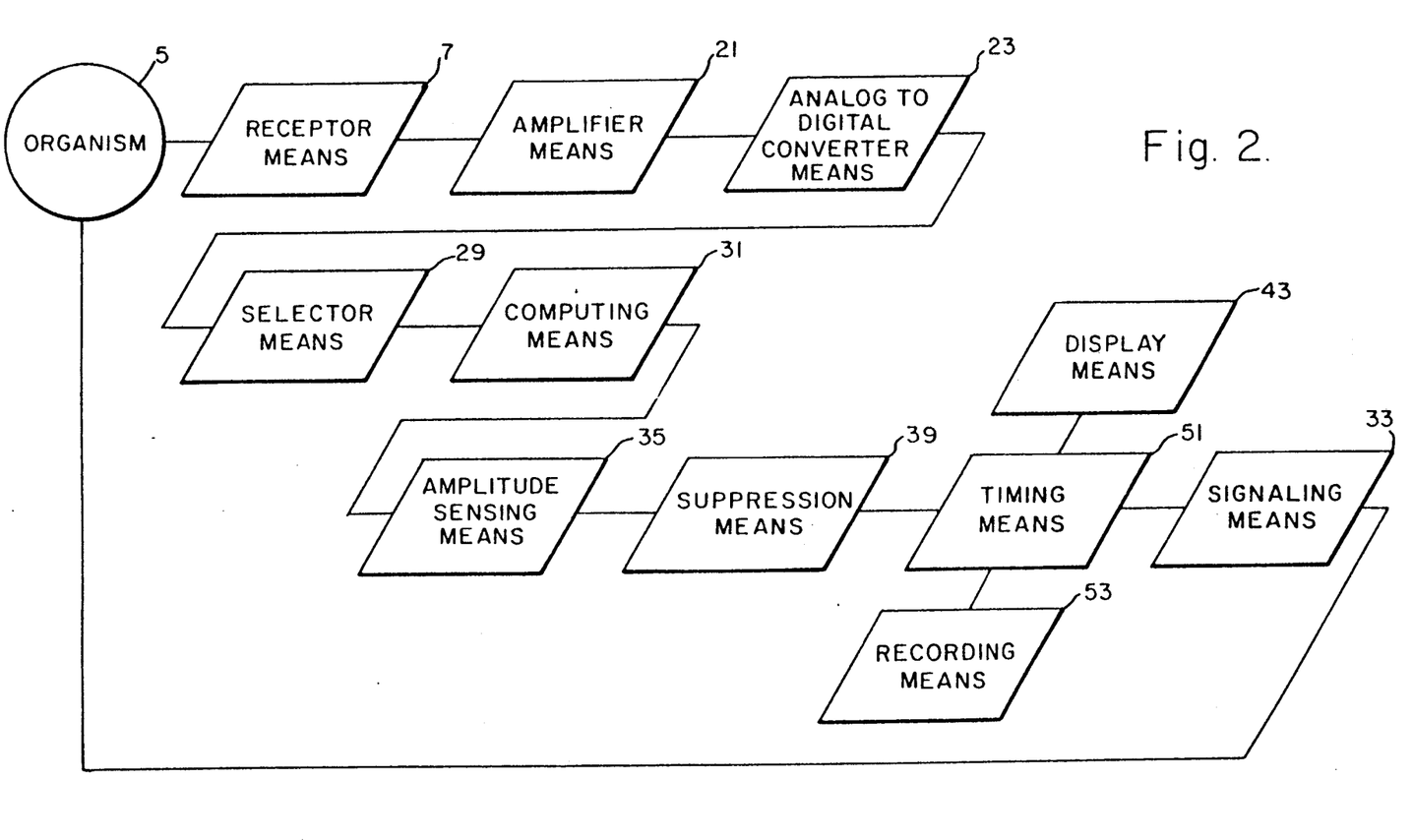
FIG. 2 is a functional block diagram of a second preferred embodiment of the improved method of the present invention.

Also, as shown in FIGS. 1 and 3, the invention can further be used without a feedback or signaling means 33 simply to accurately and easily monitor certain selected bioelectric frequencies from an organism 5 or rabbit 11 as shown. It should be indicated also, that a number of different EEG type channels can be feed into the invention for purposes of monitoring various areas provided the proper software and hardware modifications are adapted as known in the art of EEG monitoring and recording. A large number of cables, plugs, and jacks necessary for proper operation of the invention are not herein described as those accessory items are commonly known in the art of data processing with a microcomputer.

The software to be used operates with respect to the parameters as described below, as well as with the hardware described. Those skilled in the art will find the following considerations helpful.

Data collection by the software allows wrap-around in its storage, so there can be no meaning assigned to > or < in comparison of the pointers. Only = = or != are useful comparisons.

Data collection proceeds continuously whenever the system is enabled. The pointer "ad_ptr" always points to the next storage location to be used. This pointer is incremented by the interrupt handler, and is never changed by others except at the start of data collection, when it is set to the start of raw data memory.

Data filtering also proceeds continuously under most circumstances. The pointer filtered always points to the next datum to be applied to the filters. It is incremented by the collar of the filter programs, and is never changed by others except at the start of data collection or the start of data review.

Plotting may be started, stopped, reversed, restarted, etc. Two pointers are involved:

(1) "plotted", which points to the next datum to be plotted; and (2) "plotptr", which is updated by interrupt service to indicate that it is time to plot another point when plotting at normal speed. These pointers are incremented or decremented according to plotting direction: "int runn" is +1 for forward plotting, −1 for reverse, and 0 for for stopped. Thus adding "runn" to the pointer changes it appropriately.

There are a number of points to considering in constructing the program: setting up a patient file, connection to the patient, starting the program, and running the program.

Setting Up a Patient File

An example of a patient file is shown below. New files may be created and edited with a test editor which can incorporated with the system. The example file contains notes about the file contents. When a new patient file is being set up these notes can be erased from the new file.

EXAMPLE c:/adinp/adcoef
20 100 Raw data trace scale and artifact suppression level
20 30 Middle trace scale and threshold
20 20 Bottom trace scale and threshold
Notes:
 The patient's name must appear as the first line of this file.
 adcoef names a file where filter coefficients are to be found. It MUST appear as the second line of this file.
 scale and artifact suppression level must be in line 3.
 scale and threshold for the middle trace must be in line 4.
 scale and threshold for the bottom trace must be in line 5.
 Any other notes may be placed later in this file, and the file can then be read by the DOS command:

type patient

Notes can be added by use of any word processor that produces clean ASCII files, but not such as wordstar.

Starting the Program

If the computer is off, open the floppy disk drive 57 and turn the power on. The computer 27 will go through an elaborate self-testing program; then it will look to drive A: to see if it can read a disk there. If the door is open, it cannot read from drive A: so it will read the hard disk, drive C:. It will go through some more testing and loading, and finally it will show the DOS "prompt" on the screen.
C>

Insert a patient's existing disk, or create a new one, in drive A: and close the door. Type "EEG" at the keyboard and follow it with the "Enter" key.

The program can be loaded from the hard disk 55, and a file called "patient" on the floppy disk can be read. If that file is not found, the program will quit with a message stating: "Cannot find patient file."

If the necessary file is there, a display will indicate the same. The display shows the name of the patient file on line 12. This normally comes from disk drive A, so it will show: "a:patient opened.", but the system can also be set up to take the file from drive B or C, or a subdirectory of C.

The name of the patient appears on line 14 of the display, and below line 14 is scaling information and the name, size and date of the last file saved on the disk. Then, the display shows the name of the new file that will be created if you save data resulting from current session, and indicates how much more data can be placed on the disk.

The program then asks whether the information shown is correct. A separate disk for each patient, and often several disks for one patient is advisable.

If you answer yes by typing "Y", the computer 27 will go on to load more information and display a menu. If you answer "N" (or any other key) the program will allow you to change the disk or switch to a different drive or to quit.

Running the Program

The numbers representing "raw input", "low pass filtered input", and the three displayed values "top", "mid" and "bot", have multiple scaling factors applied either inherently or by intention. Below are these relationships.

Inputs in can be defined as follows:

"raw" = completely raw input to the amplifier, measured in microvolts.

"sig" = signal value after amplification, analog/digital conversion, conversion to 16 bit twos complement notation and low pass filtering. "Sig" is in arbitrary units, and 'sig' numbers will generally be larger than the corresponding number of microvolts. Sig is stored in memory and is applied to the 4–7 Hz and to the 12–15 Hz filters, which are referred to here as the middle and bottom filters.

Outputs can be defined as follows:

"top" = deflection of the top trace in response to "sig".
"mid" = deflection of the middle trace in response to the output of the middle filter when a steady state in-band signal of amplitude sign is applied.
"bot" = deflection of the bottom trace in response to the output of the bottom filter when a steady state in-band signal of amplitude sign is applied.

Scaling is important and described below. Because the middle and bottom filters may be changed and scaling may be changed, and the new filters and scales may be applied in review of existing data, it is convenient to perform scaling as part of the filtering process. Therefore, "mid" and "bot" are generated directly from the filters, ready for display, so we can also define:

"mid" = output of the middle filter with "sig" as an input.
"bot" = output of the bottom filter with "sig" as an input.

It is undesirable to alter the values of the original data by scaling. Therefore, the output of the low pass filter, "sig", is separately scaled immediately before plotting, converting it from microvolts to a trace deflection measured in pixels.

Scaling factors must be properly set. Scaling occurs, in part as a side effect of other functions, such as signal amplification, analog to digital conversion and filtering, and in part because the system operator chooses to set a scale for convenience in viewing.

The detailed system design is concerned with trace deflection measured in pixels, but the system operator is more comfortable thinking about a scale in terms of microvolts per centimeter, or some other grid unit. Therefore, a relationship is established as follows:

"grid" the number of pixels corresponding to the scale chosen by the user. A likely value is 20, so that if the user selects a scale of 50 microvolts, then a signal deflection of 50 microvolts will generate a plot deflection of 20 pixels.

The computer 27 provides for input of three scaling values from the patient file or by manual operation during a run. (The operator presses the 'F4' key and then enters three numbers.) These values are identified as:

"iscale[top]", "iscale[mid]", "iscale[bot]" which are signal levels in microvolts representing a deflection of 'grid' pixels on the display monitor 45.

Note that with a given signal, a large "iscale" generates a smaller picture. The relationship is that a trace on the monitor 45 for example of two grid units in height represents a signal of 2 "iscale" microvolts.

Other arbitrary scaling factors can be used. In order to achieve the desired scaling on the display monitor 45, in the face of other scaling factors that are not fully known or understood, a set of factors (one each for "top", "mid" and "bot") is chosen experimentally that will achieve the desired result. These values are related to the amplifier 21, the selector means 29 and possibly some other factors, but all are independent of the operator and the patient, so they are stored in a filter coefficient file and are not subject to change by the operator. They relate the arbitrary 'sig' units stored in memory to true microvolt measurements, and are called (in the computer program) "fullscal[trac]". Therefore:

$$microvolts = sig/fullscal[trace].$$

If the scale chosen by the operator is equal to the grid size, then one pixel will correspond to one microvolt. If the operator chooses a different scaling, it must be applied as well.

$$\text{top} = \frac{\text{sig}}{\text{fullscal[top]}} * \frac{\text{grid}}{\text{iscale[top]}}$$

Several factors for the top trace are combined into a signal factor. For convenience this factor is stored in the coefficient array as:

coeff[trace][16] = grid/(iscale[top] * fullscal[top])

so that the multiplication in the plotting program is:

top = sig * coeff[top][16]
  with "sig" in arbitrary units
  and "top" in pixels The "fullscal[trace]" values for the middle and bottom traces contain the same relationship of 'sig' units to microvolts and also compensate for gain of the filters. As above, the grid size and the operator selected scaling are combined with "fullscal[trace]" into a single factor. For convenience this is stored in the filter coefficient array as:

coeff[trace][16] = grid/(iscale[trace] * fullscaltrace]

These factors are applied to the datum (in 'sig' units) at the filter inputs so that the filter output is directly in pixels.

Thresholds must be established for the system. Each of the traces has an associated threshold value which leads to a decision: clamping of the filters in the case of the top trace, reward for the middle trace and inhibition of the reward for the bottom trace. Therefore, "thresh[top]", "thresh[mid]", "thresh[bot]" and decision values in microvolts, i.e., input from patient file and displayed as numbers.

For the top trace, the actual decision is based on the signal level stored in the memory in the arbitrary 'sig' units. Therefore, the top trace's microvolt threshold is converted to these units by:

sigthres = thresh[top] * fullscal[top]

For the other traces the decision is based on the filter outputs, which are already in pixels, so the microvolt thresholds are converted to pixels by:

m.thres = thresh[mid] * grid/iscale[mid]

b.thres = thresh[bot] * grid/iscale[bot]

A similar conversion is made on the top trace threshold for the purpose of graphic display of the threshold.

topthres = thresh[top] * grid/iscale[top]

These calculations of thresholds and scaling factors are made in the function 'chscale()' which are part of the module 'thrhold.c'.

Reward logic of the program is critical to proper operation. The digital filters in "philtre.asm" generate two values: "bottom.led" and "middle.led", representing the integrated amplitude of the filtered signal divided by the threshold set for that signal. (Thus a number > 1.0 means that the signal is greater than the threshold.) Indicator lights of the signaling means 33 and a counter (not shown) depend on these two values. A counter can be used to keep track of the number of times the subject has been rewarded over the test period.

Three indicator lights 38 may be provided in addition to the counter: they are referred to as red, yellow and green. Red is the inhibit indicator controlled by the undesired frequency through the 5 Hz filter and the variable "middle.led". Yellow is the enhance indicator controlled by the desired frequency. The green light signals that a reward is being posted to the counter.

The red light is turned on if "middle.led" is greater than 1.0, indicating that the 5 Hz signal exceeds the threshold. Actually, "middle.led" must become greater than 1.0 by some fixed increment to turn the red light on, and less than 1.0 by the same amount to turn the indicator off. At exactly 1.0 or very close to that value the indicator does not change. This will reduce flickering of the indicator.

The yellow light is continuously variable. Its brilliance is proportional to:

$$\frac{15 \text{ Hz integral} - \text{Threshold}}{\text{Threshold}}$$

which is equal to "bottom.led" = −1.0.

The yellow light is lighted independently of the 5 Hz inhibit signal. Both lights, however, will go off if a muscle or eye blink artifact is detected, because the inputs to the filters are clamped for one second upon detection of the artifact as part of the suppression means 39.

The green light signals a reward. When the yellow light is on continuously for 0.5 second during which the red light is off, then the green light is turned on. An audible signal is given, and the counter is incremented. The green light stays on for 0.5 second and is then, off until the next reward. The program allows time setting an interval after one reward before the next one can start to be earned, so that the frequency of rewards can be limited if desired.

Obviously, the approach described herein can be greatly modified by the clinician or the subject It should be appreciated for the foregoing description that the present invention provides an improved, more simplistic, more accurate, and less time intensive monitoring and/or control of particular bioelectric frequencies of organisms. The apparatus of the invention can be assembled from components readily available and easily assembled. Furthermore, diagnostic evaluation and patient use is greatly improved. Furthermore, the use of power spectral analysis and analog active band pass signal filtering can be eliminated.

Although the present invention has been described in detail with reference only to the presently-preferred embodiments, it will be appreciated by those of ordinary skill in the art that various modifications can be made without departing from the invention. Accordingly, the invention is limited only by the following claims.

I claim:

1. An improved method of inhibiting or facilitating analog bioelectrical frequencies in a person's body comprising the steps of:
   (a) detecting an analog bioelectrical signal at a selected location of the person's body;
   (b) amplifying said analog bioelectrical signal;
   (c) converting the analog bioelectrical signal to digital signals representing particular frequencies;
   (d) selecting a particular digital signal of interest;

(e) processing said particular digital signal of interest through a computing means using non-bandpass and non-power spectral analysis techniques and establishing an amplitude threshold voltage without delay and distortion resulting from bandpass and power spectral analysis for said particular digital signal;

(f) sending a signal to the person when said particular digital signal of interest falls within said amplitude threshold for a predetermined duration; and (g) causing the person to mentally concentrate so as to affect the amplitude of said particular digital signal of interest, thereby affecting a certain corresponding analog bioelectrical frequency emitted at said selected location of the person's body.

2. An improved method as claimed in claim 1 wherein subsequent to said step of establishing an amplitude for said particular digital signal, an additional step includes, integrating the amplitude of said selected digital signal with respect to duration and dividing a resulting value by said amplitude threshold voltage yielding a determination of whether voltage of said selected digital signal is changing, and thereby whether said analog bioelectrical frequency is being inhibited or accentuated.

3. An improved method as claimed in claim 2, further comprising the step of displaying said selected digital signal as a continuous waveform and displaying said voltage thresholds as horizontal lines associated with said continuous waveform to facilitate the determination of whether said corresponding analog bioelectrical frequency is being inhibited or accentuated.

4. An improved method as claimed in claim 3, further comprising the step of recording said digital signals on a magnetic medium of review and data manipulation.

5. An improved method as claimed in claim 1 further comprising the step of continuously displaying said particular digital signal of interest as a waveform changing with respect to time, and wherein said amplitude threshold voltage is displayed as a straight line.

6. An improved method as claimed in claim 5, further comprising the step of integrating amplitude of said particular digital signal of interest over time and dividing the integral by said amplitude threshold voltage, thereby allowing the determination of whether voltage is changing over time and whether said certain corresponding analog bioelectrical frequency is being inhibited or accentuated.

7. An improved method as claimed in claim 6, further comprising the step of suppressing extraneous signals unrelated to said analog bioelectrical signal of interest.

8. An improved method as claimed in claim 7, wherein said step of detecting an analog bioelectrical signal is achieved by using at least two electrodes positioned at said selected location of the person's body, said step of amplifying is achieved by using a signal amplifier associated with said electrodes and which recognizes voltage potential between said electrodes, said step of converting is achieved by receiving signals representing voltage variations over time and using a means for converting said voltage variation to convert said voltage variations into digital pulses, wherein said step of selecting is achieved using a means for analyzing said digital pulses which receives said digital pulses corresponding to particular analog bioelectrical frequencies, wherein said step of sending is achieved by use of a means for displaying a sensation to the person when said analog bioelectrical frequency recognized between said electrodes falls within a predetermined range for a predetermined duration, wherein said step of displaying is achieved using a waveform scroller means for displaying particular digital signals as a continuous wave over time and a monitor means for displaying said continuous wave over time as plotted by said waveform scroller means, wherein said step of integrating is achieved using a means for computing integrals, and wherein said step of recording is achieved using a means for recording said digital signals to a magnetic medium.

9. An improved method of inhibiting or facilitating analog bioelectrical frequencies in an organism body comprising the steps of:

(a) detecting an analog bioelectrical signal at a selected location of the organism;

(b) amplifying said analog bioelectrical signal;

(c) converting the analog bioelectrical signal to digital signals representing particular frequencies;

(d) selecting a particular digital signal of interest;

(e) processing said particular digital signal of interest through a computing means using non-bandpass and non-power spectral analysis techniques and establishing an amplitude threshold voltage for said particular digital signal, wherein subsequent to said step of establishing an amplitude for said particular digital signal, an additional step includes, integrating the amplitude of said selected digital signal with respect to duration and dividing a resulting value by said amplitude threshold voltage yielding a determination of whether voltage of said selected digital signal is changing without the delay and distortions associated with power spectral and bandpass analysis.

10. An improved method as claimed in claim 9, further comprising the step of displaying said selected digital signal as a continuous waveform and displaying said voltage thresholds as horizontal lines associated with said continuous waveform to facilitate the determination of whether said corresponding analog bioelectrical frequency is being inhibited or accentuated, and further comprising the step of recording said digital signals on a magnetic medium for review and data manipulation.

11. An improved method as claimed in claim 9, further comprising the step of continuously displaying said particular digital signal of interest as a waveform changing with respect to time, and wherein said amplitude threshold voltage is displayed as a straight line, and further comprising the step of integrating amplitude of said particular digital signal of interest over time and dividing the integral by said amplitude threshold voltage, thereby allowing the determination of whether voltage is changing over time and whether said certain corresponding analog bioelectrical frequency is being inhibited or accentuated.

12. An improved method as claimed in claim 11, further comprising the step of suppressing extraneous signals unrelated to said analog bioelectrical signal of interest, and wherein said step of detecting an analog bioelectrical signal is achieved by using at least two electrodes positioned at said selected location of the organism, said step of amplifying is achieved by using a signal amplifier associated with said electrodes and which recognizes voltage potential between said electrodes, said step of converting is achieved by receiving signals representing voltage variations over time and using a means for converting said voltage variation to convert said voltage variations into digital pulses, wherein said step of selecting is achieved using a means for analyzing said digital pulses which receives said digital pulses corresponding to particular analog bioelectrical frequencies, wherein said step of displaying is achieved using a waveform scroller means for displaying particular digital signals as a continuous wave over time and a monitor means for displaying said continuous wave over time as plotted by said waveform scroller means, wherein said step of integrating is achieved using a means for computing integrals, and wherein said step of recording is achieved using a means for recording said digital signals to a magnetic medium.

* * * * *